United States Patent [19]

Hunger et al.

[11] 4,150,046
[45] Apr. 17, 1979

[54] AZAMETHINE-Cu COMPLEX COMPOUNDS, PROCESS FOR THEIR PREPARATION AND THEIR USE

[75] Inventors: Klaus Hunger; Edwin Baier, both of Kelkheim, Fed. Rep. of Germany

[73] Assignee: Hoechst Aktiengesellschaft, Frankfurt am Main, Fed. Rep. of Germany

[21] Appl. No.: 875,886

[22] Filed: Feb. 7, 1978

Related U.S. Application Data

[63] Continuation-in-part of Ser. No. 815,459, Jul. 13, 1977, abandoned.

[30] Foreign Application Priority Data

| Jul. 15, 1976 | [DE] | Fed. Rep. of Germany | 2631786 |
| Nov. 25, 1976 | [DE] | Fed. Rep. of Germany | 2653483 |
| Nov. 25, 1976 | [DE] | Fed. Rep. of Germany | 2653482 |
| Nov. 25, 1976 | [DE] | Fed. Rep. of Germany | 2653481 |
| Nov. 25, 1976 | [DE] | Fed. Rep. of Germany | 2653482 |
| Nov. 25, 1976 | [DE] | Fed. Rep. of Germany | 2653483 |

[51] Int. Cl.² ............................................. C07F 1/08
[52] U.S. Cl. .............................. 260/438.1; 260/429 C
[58] Field of Search ........................ 260/438.1, 429 C

[56] References Cited

U.S. PATENT DOCUMENTS

| 2,116,913 | 5/1938 | Schmidt | 260/429 C |
| 2,282,936 | 5/1942 | Chenicek | 260/429 C |
| 3,700,709 | 10/1972 | Inman et al. | 260/429 C |
| 3,723,490 | 3/1973 | Inman et al. | 260/429 C |
| 3,891,685 | 6/1975 | Hari et al. | 260/429 C |
| 4,044,036 | 8/1977 | Hari et al. | 260/429 C |
| 4,064,349 | 12/1977 | Papenfuhs et al. | 560/56 |

Primary Examiner—Helen M. S. Sneed
Attorney, Agent, or Firm—Curtis, Morris & Safford

[57] ABSTRACT

Compounds of the formula

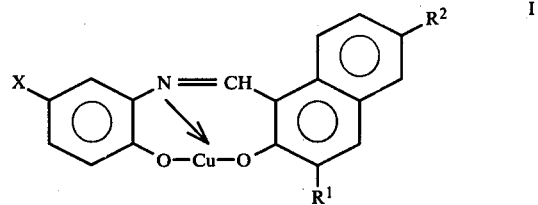

in which X is hydrogen, chlorine, bromine, alkyl of 1 to 4 carbon atoms, alkoxy of 1 to 4 carbon atoms, nitro, trifluoromethyl or a group of the formula

—COOY, wherein Y is hydrogen or alkyl of 1 to 5 carbon atoms, $R^1$ and $R^2$ are hydrogen or one of the substituents $R^1$ and $R^2$ is hydrogen and the other is —COOY, with the proviso that at least one of the substituents X, $R^1$ and $R^2$ is —COOY and that $R^2$ is hydrogen or carboalkoxy of 2 to 6 carbon atoms if X is hydrogen, are obtained by coppering the corresponding bishydroxy or phenol-anisole-compounds, are valuable pigments having clear and brilliant tints, a high heat-fastness and a high fastness to migration, especially overlacquering, to light and to weathering.

15 Claims, No Drawings

AZAMETHINE-CU COMPLEX COMPOUNDS, PROCESS FOR THEIR PREPARATION AND THEIR USE

This is a continuation-in-part of our Pat. application Ser. No. 815,459 filed July 13, 1977, now abandoned.

The present invention relates to azamethine-Cu complex compounds, to a process for preparing them and their use as pigments.

The present invention provides azamethine-Cu complex compounds of the formula I

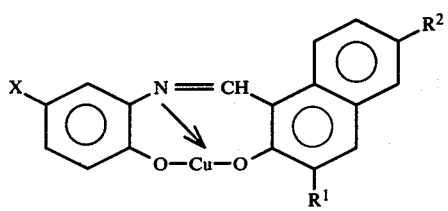

in which X represents hydrogen, chlorine, bromine, alkyl or alkoxy having 1 to 4 carbon atoms each, nitro, trifluoromethyl or a group of the formula —COOY, in which Y stands for hydrogen or alkyl having 1 to 5 carbon atoms, and $R^1$ and $R^2$ are hydrogen, or one of the radicals $R^1$ and $R^2$ is hydrogen and the other represents —COOY, with the proviso that at least one of the radicals X, $R^1$ and $R^2$ stands for -COOY and that $R^2$ is hydrogen or carboalkoxy of 2 to 6 carbon atoms if X is hydrogen. Preferred are compounds of the above formula, in which X is chlorine, bromine, alkyl of 1 to 4 carbon atoms, alkoxy of 1 to 4 carbon atoms, nitro, trifluoromethyl or a group of the formula

—COOY, wherein Y is hydrogen or alkyl of 1 to 5 carbon atoms, $R^1$ and $R^2$ are hydrogen or one of the substituents $R^1$ and $R^2$ is hydrogen and the other is —COOY, with the proviso that at least one of the substituents X, $R^1$ and $R^2$ is —COOY; furthermore, compounds wherein X is —COOY and $R^1$ and $R^2$ are hydrogen; and, moreover, compounds in which X is chlorine, bromine, alkyl of 1 to 4 carbon atoms, alkoxy of 1 to 4 carbon atoms, nitro, trifluoromethyl or a group of the formula

—COOY, wherein Y is hydrogen or alkyl of 1 to 5 carbon atoms, and one of the substituents $R^1$ and $R^2$ is hydrogen and the other is —COOY.

If Y represents alkyl, it stands for example for ethyl, n-propyl, isopropyl, n-butyl, isobutyl, n-amyl or iso-amyl, however, preferably for methyl.

The invention also provides a process for the preparation of the compounds of the formula I, which comprises metallizing an azamethine of the formula II

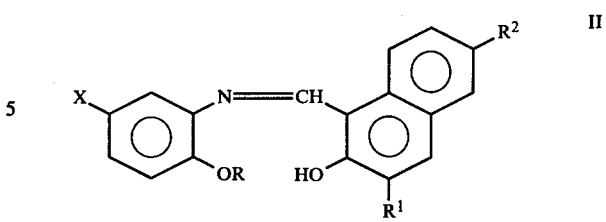

wherein R is hydrogen or a methyl group, with a copper-yielding compound, i.e. an inorganic or organic, preferably bivalent copper salt, as well as their use as pigments.

As copper salts, there are suitable, for example, copper(II)-chloride, copper(II)sulfate, copper formate, copper(II)acetate or copper stearate.

The coppering of the compound II, in which R stands for hydrogen, may be carried out in water or organic solvents or aqueous-organic solvents at a temperature in the range of from 20 to 180° C., preferably from 20 to 150° C., especially from 80 to 110° C. As solvents for the coppering there are suitable, for example, alcohols, especially lower alkanols, such as methanol, ethanol, n-propanol, isopropanol, n-butanol or isobutanol; glycol-monomethylether; glacial acetic acid; formamide or dipolar aprotic solvents, such as dimethylformamide, N-methylpyrrolidone or tetramethylene-sulfone. For the coppering reaction, use is made preferably of the same solvent, in which the copper salt has previously been dissolved. The coppering may be effected in the presence of a basic compound, such as sodium acetate.

The coppering of the anisole derivatives ($R=CH_3$) is carried out in the presence of a coppering agent in an inert organic solvent at a temperature in the range of from 120 to 180° C. with desalkylation, to give the azamethine compound of the formula I.

The azamethine compound of the formula II is prepared either separately, or the azamethine-Cu complex of the formula I is synthesized in a single reaction without isolating intermediate products.

The compounds of the formula II are prepared by a condensation of the corresponding 2-aminophenol or -anisole or their hydrochlorides with the 2-hydroxynaphthaldehyde-(1) optionally substituted in the 3- or 6-position by the group —COOY, Y optionally also being a cation, for example an alkali metal, in which process equivalent amounts of the two starting compounds are reacted in water, organic solvents or aqueous-organic solvents at a temperature in the range of from 20 to 150° C., preferably from 80 to 110° C.

The reaction may also be effected under an inert gas cover, such as in a nitrogen atmosphere. If the reaction is carried out in water, the addition of surface-active agents, such as cationic, anionic or non-ionogenic compounds, is recommended. If the hydrochloride of the 4-carbomethoxy-2-aminophenol or -anisole is used, a basic compound, for example, sodium acetate, sodium hydrogencarbonate or potassium carbonate, should be added. As organic solvents there are mentioned, for example: lower alcohols having 1 to 6 carbon atoms, glacial acetic acid, dimethylformamide or glycol-monomethylether. After isolation and washing, the compound of the formula II obtained may then be coppered as has been described above. According to another process the azamethine copper complex of the formula I can be prepared directly in a grinding device, in which the starting compounds, for example, 4-carbomethoxy-2-aminophenol and 2-hydroxynaphthaldehyde-(1), are ground in water together with a coppering agent, for example, copper(II)-sulfate in the presence of an acid buffer, such as sodium acetate. As grinding devices there are suitable, for example, ball mills, bead mills or sand mills. The grinding may also be carried out in the presence of a salt and/or a surface-active agent.

The azamethine-copper complex compounds of the formula I have valuable properties as pigments.

In order to obtain optimum coloristic properties of the pigments of the invention, it is sometimes advantageous to convert the ready pigment into a finely divided form by heating it in a solvent, optionally in the presence of water or salt solutions.

As solvents suitable for this purpose there may be mentioned those in which the pigment is insoluble, however, which promote under the finishing conditions a certain superficial dissolving action, for example, aliphatic alcohols, especially lower alkanols, such as ethanol, isopropanol, iso- or n-butanol, chloro-aromatic compounds, such as chlorobenzene and -toluene, or dichlorobenzenes, as well as dipolar aprotic solvents, for example, dimethylformamide, dimethylacetamide, dimethylsulfoxide, N-methyl-pyrrolidone, polyalkylureas, such as tetramethylurea, and phosphoric acid amides, such as hexamethyl-phosphoric acid-trisamide.

Also a fine division by grinding with salts or solvents may be advantageous, in which process in the former case a dry grinding in vibration grinding mills is preferably effected and the salt is subsequently extracted with water, whereupon a wet grinding or a temperature treatment with solvents may optionally follow.

As salts there may be mentioned essentially alkali metal and alkaline earth metal salts of hydrohalic acids or of sulfuric acid, for example, sodium or potassium chloride, as well as sodium or magnesium sulfate.

The solvents which may be used for the wet grinding process are essentially those mentioned above, for example, alcohols, acid amides or dimethyl sulfoxide.

The novel compounds represent valuable pigments which are used in printing inks, dispersion dyes, varnishes, and which are suitable for pigmenting high-molecular-weight organic material, for example, cellulose ethers and esters, polyamides, polyurethanes or polyesters, acetyl cellulose, nitrocellulose, natural resins or plastics, for example, aminoplasts, especially urea and melamine formaldehyde resins, alkyd resins, phenoplasts, polycarbonates, polyolefins, such as polyethylene or polypropylene, polystyrene, polyvinylchloride, polyacrylonitrile, polyacrylic acid esters, rubber, casein, silicones and silicone resins. It is unimportant whether the above-mentioned high-molecular-weight compounds are present as plastic masses, melts, or in the form of spinning solutions, lacquers or printing pastes. Depending on the application, it may be advantageous to use the novel pigments as toners or in the form of preparations.

The pigments of the invention have a high color intensity (tinctorial strength), a pure color shade, a good fastness to high temperatures in stove-enamels and plastics, however, particularly an excellent fastness to overlacquering, to light and to weather, an extremely high fastness to light and to weathering, especially under the extreme conditions of an aluminum metallic lacquering.

The following Examples serve to illustrate the invention, the percentages being by weight, unless otherwise stated.

EXAMPLE 1

17.2 Grams of 2-hydroxynaphthaldehyde-(1) are suspended in 200 ml of ethanol, are heated to boiling temperature with 21.5 g of the hydrochloride of 4-carbomethoxy-2-aminophenol and 10 g of anhydrous sodium acetate in 200 ml of ethanol, and the reaction mixture is maintained at this temperature for 1 hour. During the reaction time, nitrogen is led over the mixture. The orange-red precipitate of the azamethine is suction-filtered and washed with ethanol and water. Yield (after drying) :29.4 g (91.6% of the theory).

16 Grams of the azamethine thus obtained are dissolved in 150 ml of dimethylformamide and are treated for 3 hours at 100° C. with 10 g of copper(II)acetate. The mixture is cooled to 50° C., is suction-filtered, and the yellow pigment is washed with ethanol and water. After drying, 17.8 g of the compound of the formula

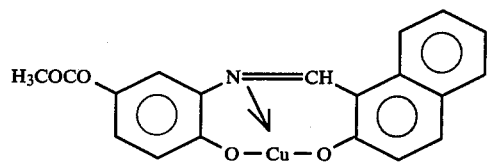

are obtained.

EXAMPLE 2

16.7 Grams of 4-carbomethoxy-2-aminophenol and 17.2 g of 2-hydroxynaphthaldehyde-(1) are stirred for 5 minutes in 100 ml of water. Subsequently 50 ml of 2N sodium hydroxide solution and 30 ml of a 40% sodium hydrogensulfite solution are added, and the mixture is stirred for 15 minutes at 95° C. The precipitate is filtered off with suction and is washed with cold water. The press cake is then stirred in 200 ml of water with an impeller.

Subsequently a solution of 27.5 g of copper(II)sulfate pentahydrate in 100 ml of water and 50 g of concentrated ammonia solution are added, the mixture is heated to 95° C. and is maintained at this temperature for 1 hour. The pigment is filtered off with suction, while hot, is washed with hot water and dried. 32.9 Grams of the compound of Example 1 are obtained.

EXAMPLE 3

A mixture of 16.7 g of 4-carbomethoxy-2-aminophenol, 17.2 g of 2-hydroxynaphthaldehyde-(1) and 200 ml of water is ground in a ball mill with 200 g of ceramic balls (diameter of 10 mm) for 24 hours. Upon adding 25 g of sodium acetatetrihydrate, 26 g of copper(II)sulfate pentahydrate and 100 ml of water, the mixture is continued to be ground for another 80 hours. The ground product obtained is washed with water and dried. Yield: 35.7 g of the yellow pigment of Example 1.

EXAMPLE 4

16.7 Grams of 4-carbomethoxy-2-aminophenol and 17.2 g of 2-hydroxynaphthaldehyde-(1) are dispersed with 400 ml of water by means of an impeller, and the dispersion is heated to a temperature in the range of from 95 to 98° C. and maintained at this temperature for 4 hours.

The product is suction-filtered, washed with hot water, and the moist press cake is stirred with 400 ml of water in which 26 g of copper(II)sulfate pentahydrate and 25 g of sodium acetate are dissolved; thereafter the mixture is heated to boiling temperature. After is has been heated to 100° C for 5 hours, the product is filtered off with suction, while hot, is washed with water dried. 34.9 Grams of the yellow pigment of Example 1 are obtained.

EXAMPLE 5

18.1 Grams of 4-carbomethoxy-2-aminoanisole and 17.2 g of 2-hydroxynaphthaldehyde-(1) are heated in 400 ml of diethyleneglycol-monomethylether to 100°C. and are maintained at this temperature for 2 hours. During the reaction time, nitrogen is led over the mixture. 10 Grams of copper(II)acetate dissolved in 100 ml of diglycol-monomethylether are added to the hot reaction mixture. Said mixture is heated to 150° C. and is maintained at this temperature for 4 hours. After cooling, the yellow pigment is filtered off with suction, is thoroughly washed with ethanol and water and dried. 31.9 Grams of the compound of Example 1 are obtained.

EXAMPLE 6

17.2 Grams of 2-hydroxy-1-naphthaldehyde are suspended in 700 ml of n-propanol. Thereafter 24.3 g of the hydrochloride of 3-amino-4-hydroxybenzoic acid-n-propylester and 10 g of anhydrous sodium acetate are added. The mixture is refluxed for 2 hours under a nitrogen atmosphere. The yellow azamethine of the formula

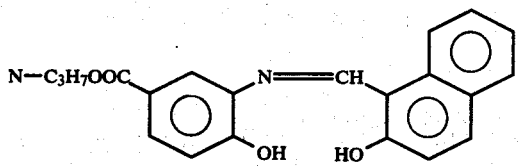

is suction-filtered, while hots, is washed with n-propanol and water and dried. Yield: 33 Grams.

17.5 Grams of the azamethine thus prepared are suspended in 250 ml of n-propanol. Subsequently 12.5 g of copper(II)-sulfate-pentahydrate dissolved in 30 ml of water are added dropwise within 15 minutes. The pH value is maintained at 5 by adding about 25 ml of a 4N sodium acetate solution. The mixture is then heated under reflux for 3 hours under a nitrogen atmosphere, subsequently the product is suction-filtered, while hot, is washed with n-propanol and water and dried. 23.3 Grams of the green pigment of the formula

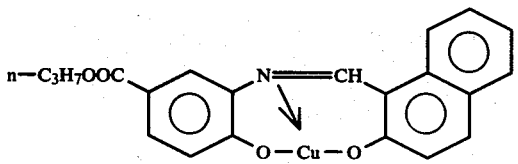

are obtained.

EXAMPLE 7

17.2 Grams of 2-hydroxy-1-naphthaldehyde are suspended in 500 ml of ethanol. Subsequently 23 g of the hydrochloride of 3-amino-4-hydroxybenzoic acid ethylester and 10 g of anhydrous aodium acetate are added. The mixture is boiled under reflux for 2 hours in a nitrogen atmosphere. The precipitated orange azamethine of the formula

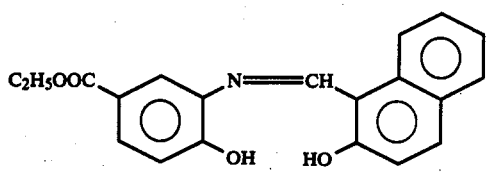

is filtered off with suction, while hot, is washed with ethanol and water and dried. Yield: 28.4 Grams. 16.75 Grams of the azamethine thus prepared are suspended in 250 ml of ethanol and are coppered, as has been described in Example 6. 24 Grams of the green pigment of the formula

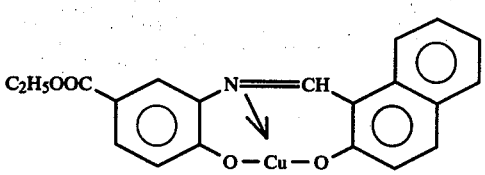

are obtained.

EXAMPLE 8

17.2 Grams of 2-hydroxy-1-naphthaldehyde are suspended in 500 ml of n-butanol, thereafter 25.75 g of the hydrochloride of 3-amino-4-hydroxybenzoic acid n-butylester and 10 g of anhydrous sodium acetate are added. The mixture is heated to 90° C and is maintained at this temperature for 2 hours. Subsequently the product is filtered off with suction at about 70° C, is washed with n-butanol and water and dried. 26.55 Grams of the orange azamethine of the formula

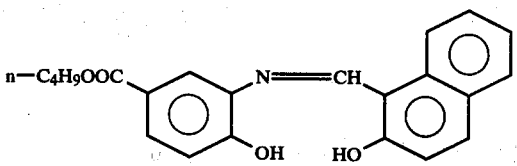

are obtained.

18.15 Grams of the azamethine thus obtained are suspended in 250 ml of n-butanol and are coppered according to the method described in Example 6. 19.95 Grams of the yellowish-green pigment of the formula

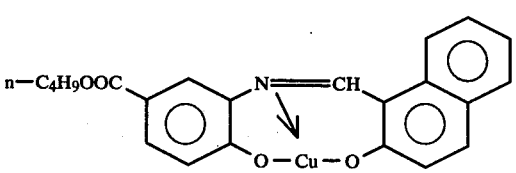

are obtained.

In a manner analogous to that described in Examples 6 through 8, the following pigments were obtained:

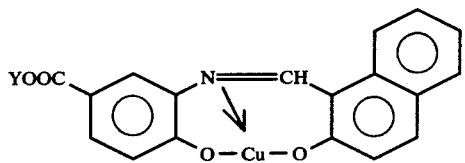

| Example | Y | ColorShade in book-printings |
|---|---|---|
| 9 | H | greenish-yellow |
| 10 | H₃C\CH—  H₃C/ | greenish-yellow |
| 11 | H₃C\CH—CH₂—  H₃C/ | reddish-yellow |
| 12 | CH₃<br>\|<br>CH₃—CH₂—CH— | brownish-yellow |
| 13 | CH₃—CH₂—CH₂—CH₂—CH₂— | reddish-yellow |
| 14 | CH₃<br>\|<br>CH₃—CH₂—CH—CH₂— | brownish-yellow |

EXAMPLE 15

21.6 Grams of 2-hydroxy-1-naphthaldehyde-3-carboxylic acid are refluxed together with 11.4 g of o-aminophenol in 300 ml of ethanol under a nitrogen atmosphere. Then the precipitate of the azamethine is suction-filtered, while hot, is washed with ethanol and water and dried. 10.2 Grams of the orange azamethine thus prepared are suspended in 300 ml of ethanol and are then heated to boiling temperature together with 7 g of copper acetate and maintained at the boil for 3 hours. The pH value is maintained at 6.5 by adding 25 ml of 4N sodium acetate solution. The product is suction-filtered, while hot, is washed with ethanol and water and dried. Yield: 11.7 Grams of the greenish-yellow pigment of the formula

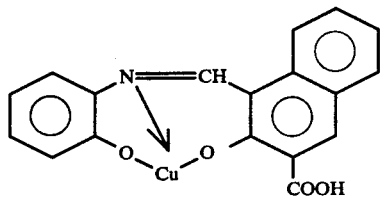

EXAMPLE 16

21.6 Grams of 2-hydroxy-1-naphthaldehyde-3-carboxylic acid are suspended together with 11.4 g of o-aminophenol in 300 ml of glacial acetic acid. The suspension is heated to the boiling point and is maintained at this temperature for 3 hours. The product is filtered off with suction, while hot, and is washed with ethanol and water. After drying, 29.9 g of the orange azamethine of the formula

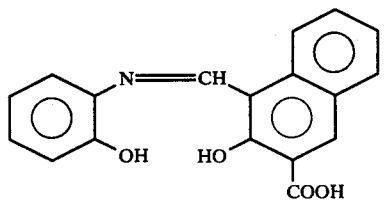

are obtained.

15.35 Grams of the azamethine thus prepared are dissolved in 100 ml of dimethylformamide and are heated with 100 ml of diethylene-glycol-dimethylether and 15 g of copper acetate to 100° C; then the mixture is maintained at this temperature for 3 hours. 17.2 Grams of the greenish-yellow pigment of the formula

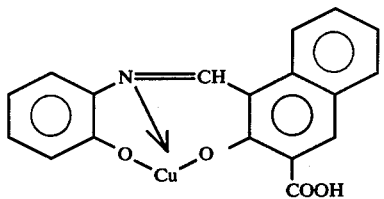

are obtained.

EXAMPLE 17

If the process is carried out according to the method described in Example 16, however, while using 23.2 g of the corresponding methylester instead of the 2-hydroxy-1-naphthaldehyde-6-carboxylic acid, 29.7 g of the orange azamethine of the formula

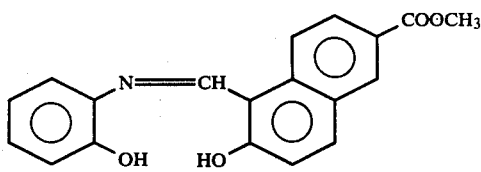

are obtained.

20 Grams of the azamethine are dissolved in a mixture of 150 ml of dimethylformamide and 150 ml of diethylene-glycoldimethylether and are heated with 13.5 g of copper(II)sulfate pentahydrate to 100° C and maintained at this temperature for 3 hours. The product is then suction-filtered, while hot, is washed with ethanol and water and dried.

12 Grams of this crude pigment are ground for 10 hours together with 50 g of sodium sulfate and 50 g of sodium acetate in a porcelain ball mill with 800 g of porcelain balls having a diameter of 10 mm. The contents of the mill are stirred in hot water, the greenish-yellow pigment is isolated which is then washed until it is free from salt and dried.

EXAMPLE 18

If the process is carried out as has been described in Example 17, however, while replacing the 2-hydroxy-1-naphthaldehyde-6-carboxylic acid-methylester by 24.8 g of 2-hydroxy-1-naphthaldehyde-3-carboxylic acid-ethylester, 31.5 g of the azamethine of the formula

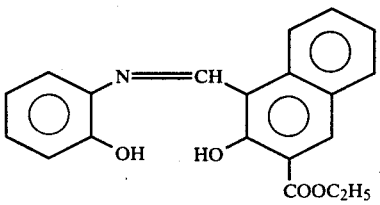

are obtained.

15.4 Grams of the azamethine thus prepared are heated to 100° C. with 100 ml of dimethylformamide and 100 ml of diethylene-glycol-dimethylether and 9 g of copper acetate, and the mixture is maintained at this temperature for 3 hours. Subsequently the product is filtered off with suction, while hot, is washed with dimethylformamide, methanol and water and dried. 16.3 Grams of the yellowish-green azamethine-Cu complex compound of the formula

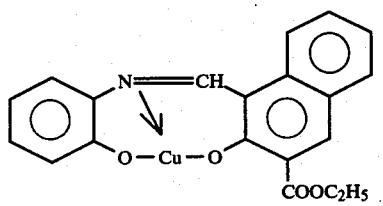

are obtained.

According to the method described in Example 15 through 18, the following further azamethine-Cu complex compounds are obtained:

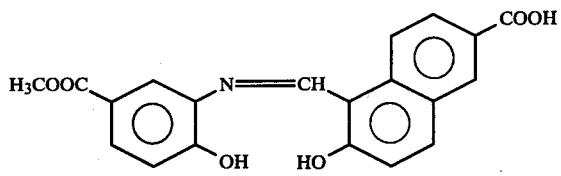

are obtained.

20 Grams of the azamethine are dissolved in a mixture of 150 ml of dimethylformamide and 150 ml of diethylene-glycoldimethylether and are heated to 100° C. with 15 of copper(II)-sulfate pentahydrate, the mixture being maintained at this temperature for 3 hours. Subsequently the product is suction-filtered, while hot, is washed and ethanol and water and dried. Yield: 23.5 Grams of the greenish-yellow pigment of the formula

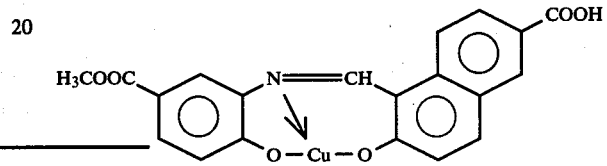

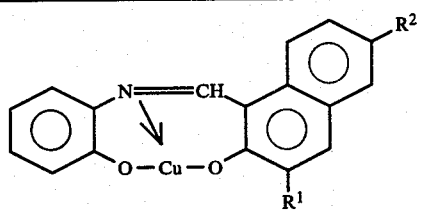

| Example | R$^1$ | R$^2$ | Color Shade |
|---|---|---|---|
| 19 | COOCH$_3$ | H | greenish-yellow |
| 20 | COO-nC$_3$H$_7$ | H | greenish-yellow |
| 21 | COO-n-C$_4$H$_9$ | H | greenish-yellow |
| 22 | COOCH(CH$_3$)$_2$ | H | yellow |
| 23 | COOCH(CH$_3$)—CH$_2$CH$_3$ | H | yellow |
| 24 | COO-n-C$_5$H$_{11}$ | H | greenish-yellow |
| 25 | COO—CH$_2$CH(CH$_3$)—CH$_2$CH$_3$ | H | yellow |
| 26 | H | COOC$_2$H$_5$ | greenish-yellow |
| 27 | H | COO-n-C$_3$H$_7$ | greenish-yellow |
| 28 | H | COO-n-C$_4$H$_9$ | greenish-yellow |
| 29 | H | COO—CH(CH$_3$)$_2$ | greenish-yellow |
| 30 | H | COO-n-C$_5$H$_{11}$ | greenish-yellow |
| 31 | H | COOCH(CH$_3$)—CH$_2$—CH$_3$ | yellow |
| 32 | H | COOCH$_2$CH(CH$_3$)—CH$_2$—CH$_3$ | greenish-yellow |

EXAMPLE 33

21.6 Grams of 2-hydroxy-1-naphthaldehyde-6-carboxylic acid are suspended with 21.5 g of the hydrochloride of 3-hydroxy-4-aminobenzoic acid-methylester in 300 ml of glacial acetic acid. The mixture is heated to the boiling point and is maintained at this temperature for 3 hours. The product is filtered off with suction, while hot, is washed with ethanol and water. After drying, 35.2 g of the orange azamethine of the formula 12 Grams of this crude pigment are ground for 10 hours together with 50 g of sodium sulfate and 50 g of sodium acetate in a porcelain ball mill with 800 g of porcelain balls having a diameter of 10 mm. The contents of the mill are then stirred in hot water, the greenish-yellow pigment is isolated, washed until it is saltfree and dried.

EXAMPLE 34

If the process is carried out as has been described in Example 33, however, while replacing the 2-hydroxy-1naphthaldehyde-6-carboxylic acid by 2-hydroxy-1-naphthaldehyde-3-carboxylic acid, 35.75 g of the azamethine of the formula

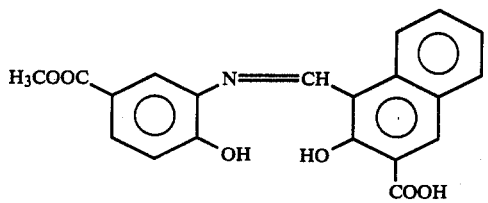

are obtained. 18.3 Grams of the azamethine thus prepared are heated to 100° C. with 100 ml of dimethylformamide and 100 ml of diethylene-glycol-dimethylether and 10 g of copper acetate, and the mixture is maintained at this temperature for 3 hours. Subsequently the product is filtered off with suction, while hot, is washed with dimethylformamide, ethanol and water and dried. 17.3 Grams of the yellowish-green azamethine-Cu complex compound of the formula

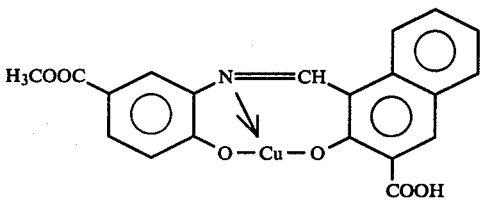

are obtained.

In a manner analogous to that described in Examples 33 and 34, the following further azamethine-Cu complex compounds are obtained:

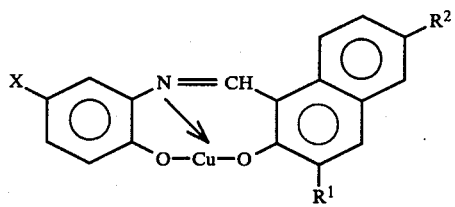

| Ex. | X | $R_1$ | $R_2$ | Color Shade |
|---|---|---|---|---|
| 35 | Cl | COOH | H | reddish-brown |
| 36 | Cl | H | COOH | yellow |
| 37 | $NO_2$ | COOH | H | reddish-yellow |
| 38 | $NO_2$ | H | COOH | reddish-yellow |
| 39 | Br | COOH | H | greenish-yellow |
| 40 | Br | H | COOH | brownish-yellow |
| 41 | $COOC_2H_5$ | COOH | H | yellowish-green |
| 42 | $COOC_2H_5$ | H | COOH | green |
| 43 | $COOC_3H_7(n)$ | COOH | H | brownish-green |
| 44 | $COOC_3H_7(n)$ | H | COOH | yellowish-green |
| 45 | COOCH(CH$_3$)$_2$ | COOH | H | brownish-green |
| 46 | COOCH(CH$_3$)$_2$ | H | COOH | yellowish-green |
| 47 | $COOC_4H_9(n)$ | COOH | H | yellowish-green |
| 48 | $COOC_4H_9(n)$ | H | COOH | bluish-green |
| 49 | $CH_3$ | COOH | H | reddish-yellow |
| 50 | $CH_3$ | H | COOH | reddish-yellow |
| 51 | $CF_3$ | COOH | H | yellowish-green |

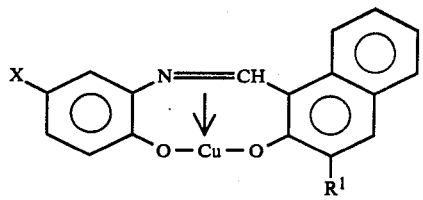

| Ex. | X | $R_1$ | $R_2$ | Color Shade |
|---|---|---|---|---|
| 52 | $CF_3$ | H | COOH | yellow |
| 53 | $OCH_3$ | COOH | H | brownish-yellow |
| 54 | $OCH_3$ | H | COOH | reddish-yellow |
| 55 | Cl | $COOCH_3$ | H | reddish-yellow |
| 56 | $NO_2$ | H | $COOCH_3$ | reddish-yellow |
| 57 | $CO_2CH_3$ | H | $COOCH_3$ | yellow |
| 58 | COOH | COOH | H | greenish-yellow |
| 59 | COOH | H | COOH | greenish-yellow |

We claim:
1. A compound of the formula

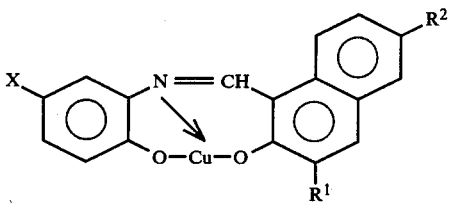

in which X is hydrogen, chlorine, bromine, alkyl of 1 to 4 carbon atoms, alkoxy of 1 to 4 carbon atoms, nitro, trifluoromethyl or carboalkoxy of 2 to 6 carbon atoms, $R^1$ and $R^2$ are hydrogen or one of the substituents $R^1$ and $R^2$ is hydrogen and the other is —COOY wherein Y is hydrogen or alkyl of 1 to 5 carbon atoms, with the proviso that at least one of the substituents $R^1$ and $R^2$ is -COOY and that $R^2$ is hydrogen or carboalkoxy of 2 to 6 carbon atoms if X is hydrogen.

2. A compound of the formula

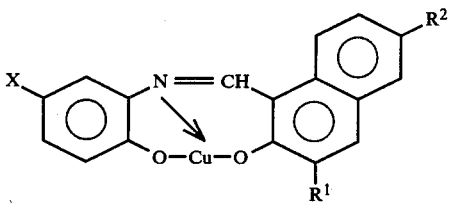

wherein X is chlorine, bromine, alkyl of 1 to 4 carbon atoms, alkoxy of 1 to 4 carbon atoms, nitro, trifluoromethyl or carboalkoxy of 2 to 6 carbon atoms, $R^1$ and $R^2$ are hydrogen or one of the substituents $R^1$ and $R^2$ is hydrogen and the other is -COOY wherein Y is hydrogen or alkyl of 1 to 5 carbon atoms, with the proviso that at least one of the substituents $R^1$ and $R^2$ is —COOY.

3. A compound as defined in claim 1, wherein X is carboalkoxy of 2 to 6 carbon atoms and $R^1$ and $R^2$ are hydrogen.

4. The compound as defined in claim 3, wherein X is carbomethoxy.

5. The compound as defined in claim 3, wherein X is carboethoxy.

6. The compound as defined in claim 3, wherein X is carbo-n-propoxy.

7. The compound as defined in claim 3, wherein X is carbo-n-butoxy.

8. A compound as defined in claim 1, wherein X is chlorine, bromine, alkyl of 1 to 4 carbon atoms, alkoxy of 1 to 4 carbon atoms, nitro, trifluoromethyl or carboalkoxy of 2 to 6 carbon atoms, and one of the substituents $R^1$ and $R^2$ is hydrogen and the other is —COOY wherein Y is hydrogen or alkyl of 1 to 5 carbon atoms.

9. The compound as defined in claim 1, wherein X is carbomethoxy, $R^1$ is carboxy and $R^2$ is hydrogen.

10. The compound as defined in claim 1, wherein X is carboethoxy, $R^1$ is carboxy and $R^2$ is hydrogen.

11. The compound as defined in claim 1, wherein X is carboisopropoxy, $R^1$ is carboxy and $R^2$ is hydrogen.

12. The compound as defined in claim 1, wherein X is carbomethoxy, $R^1$ is hydrogen and $R^2$ is carboxy.

13. The compound as defined in claim 1, wherein X is carbo-n-propoxy, $R^1$ is hydrogen and $R^2$ is carboxy.

14. A compound as defined in claim 1, wherein X and $R^1$ are hydrogen and $R^2$ is carboalkoxy of 2 to 6 carbon atoms.

15. A compound as defined in claim 1, wherein X and $R^2$ are hydrogen and $R^1$ is —COOY.

* * * * *